United States Patent [19]

Ritter

[11] Patent Number: 4,675,433

[45] Date of Patent: Jun. 23, 1987

[54] MONO AND BIS (METH)-ACRYLATES, AND USES THEREOF

[75] Inventor: Wolfgang Ritter, Hilden, Fed. Rep. of Germany

[73] Assignee: Henkel Kommanditgesellschaft auf Aktien, Duesseldorf, Fed. Rep. of Germany

[21] Appl. No.: 802,543

[22] Filed: Nov. 27, 1985

Related U.S. Application Data

[63] Continuation-in-part of Ser. No. 726,278, Apr. 24, 1985, abandoned, which is a continuation of Ser. No. 460,900, Jan. 25, 1983, abandoned.

[30] Foreign Application Priority Data

Feb. 10, 1982 [DE] Fed. Rep. of Germany ....... 3204504

[51] Int. Cl.$^4$ .............................................. C08F 8/42
[52] U.S. Cl. .................... 560/55; 560/126; 560/182; 528/271
[58] Field of Search ............... 560/182, 55, 126; 528/271, 361, 392

[56] References Cited

U.S. PATENT DOCUMENTS

| | | | |
|---|---|---|---|
| 3,066,112 | 11/1962 | Bowen | 260/41 |
| 3,179,623 | 4/1965 | Bowen | 260/47 |
| 3,336,418 | 8/1967 | Dill | 560/182 |
| 3,810,938 | 5/1974 | Schmitt et al. | 260/486 R |
| 4,131,729 | 12/1978 | Schmitt et al. | 526/282 |
| 4,292,231 | 9/1981 | Gabriel et al. | 528/392 |
| 4,378,457 | 3/1983 | Gurber et al. | 528/361 |

OTHER PUBLICATIONS

J. Dent. Res. 49, 810 (1970).
J. Dent. Res. 52, 731 (1973).
J. Dent. Res. 52, 1128 (1973).
Polymer Science and Technology 14, 357, 373 and 379 (1981).
J. Dent. Res. 58, 1544 and 1981 (1971).
J. Dent. Res. 58, Abstr. No. 1216, 395 (1979).

*Primary Examiner*—Joseph L. Schofer
*Assistant Examiner*—Peter D. Mulcahy
*Attorney, Agent, or Firm*—Ernest G. Szoke; Henry E. Millson, Jr.

[57] ABSTRACT

(Meth)-acrylate compounds having one or two terminal (meth)-acrylic acid groups on an oligomer chain which have low volatility and are liquid to solid at room temperature, wherein the oligomer chain is mainly in the form of a polyester oligomer formed from one or more hydroxycarboxylic acids. The preferred (meth)-acrylate compounds are based on polyester-oligomers with a mean molecular weight in the range of about 200 to 600. The invention also relates to the use of these new reactive (meth)-acrylate compounds in construction adhesives.

35 Claims, No Drawings

MONO AND BIS (METH)-ACRYLATES, AND USES THEREOF

This is a continuation-in-part of pending application Ser. No. 726,278 filed April 24, 1985 now abandoned, which is a continuation of application Ser. No. 460,900 filed on Jan. 25, 1983, now abandoned.

BACKGROUND OF THE INVENTION

Within the group of reactive adhesives the methacrylate systems are becoming increasingly important. They have been commercially available for years as a two component formulation. Component A (adhesive component) usually exists as a solution of elastomers in a monomer or a monomer mixture based on acrylic acid and/or especially methacrylic acid. Component B (activator or hardener component) contains an initiator to initiate free radical polymerization.

Both components prior to their use are thoroughly mixed together, thereby starting the polymerization of the monomers.

A further development of the so-called two component systems are the "No-Mix" or "Second Generation Acrylate adhesives". The use of these adhesives is similar to that of the contact adhesives, i.e. the initiator component is first applied as a thin layer on one or both of the surfaces to be glued together. After a waiting period, which can be up to several hours, the adhesive component is then applied. The bonding is carried out by fixing the components in the desired position.

In the adhesive component polymerizable monomers can be used alone or in combination, especially methacrylic acid or a methacrylic acid derivative such as methyl methacrylate, or suitable acrylic acid compounds, e.g. butyl acrylate. In addition to these monomers, other systems were investigated, which to some extent have gained a measure of technical importance. Examples of these are: ethylene glycol dimethacrylate and oligoethylene glycol dimethacrylates, (meth)-acrylic ester of tricyclo[5.2.1.0$^{2,6}$] decane, glycerine (meth-)acrylate, bisphenol-A-derivatives, perfluoborated dimethacrylates, aromatic diester-dimethacrylates, aromatic diether dimethacrylates and aromatic ester ether dimethacrylates, urethane dimethacrylates, diurea dimethacrylates, and other compounds. From the vast relevant literature, the following are mentioned as examples thereof: Polymer Science and Technology 14, 357, 373 and 379 (1981); J. Dent. Res. 58, 1544 and 1981 (1979), J. Dent. Res. 58, Abstr. No. 1216, 395 (1979), J. Dent. Res. 49, 810 (1970) and 52, 731 as well as 1128 (1973), U.S. Pat. Nos. 4,131,729, 3,066,112, 3,179,623, 3,810,938 as well as German Application Nos. 2,432,013, 2,312,559 and 2,411,760. In order to improve cohesion, to adjust to suitable viscosity for application purposes, and to reduce the volume contraction during hardening, polymers are mixed with the monomers in the adhesive component. Examples thereof are polymethylmethacrylates, polychloroprene, chlorosulfonated polyethylene, nitrile rubbers and/or polyurethanes.

The classical hardeners for room temperature polymerizable methacrylate systems consist of benzoyl peroxide as the initiator and tertiary aromatic amines, especially N,N-diemthyltoluidine, as the accelerator.

Today there is a broad pallet of accelerators at our disposal. Also of importance are, in this connection, new hardener systems based on organoboron compounds, which when exposed to oxygen in the air will initiate the polymerization reaction, thereby making them particularly suitable for work at room temperature. New hardening systems based on such organoboron compounds are the subject matter of a number of prior patent applications of the applicant.

Reaction adhesives of the organoboron type exhibit a number of useful properties. For example, they exhibit a broad spectrum of applications for various surfaces with little requirements for pretreatment of the surfaces, they harden quickly if desired even at room temperature, and through the proper selection of reactive monomers or monomer mixtures they can be adjusted to give good flexibility values for the adhesive layer. High stress shearing strengths can be obtained. When working with these adhesives, the so-called open time can be regulated. The adhesive bond will exhibit less shrinkage and good reproducibility, while exhibiting good resistance to solvents and temperatures.

The dominant constituents of the adhesive components are still mono(meth)-acrylates, which exhibit high vapor pressure. However, the use thereof not only causes an offensive odor, but consequently the adhesive component, for example for No-Mix applications, can only be stored open for a short while.

Bismethacrylates normally have higher boiling points. A number of these types, especially bismethacrylates with high molecular weight, are normally solid and therefore can be used as monomers in adhesives to only a minor extent. Furthermore, with respect to bismethacrylates with low molecular weights, the distance between the functional groups is small and the corresponding polymers are highly cross linked and have a tendency to become brittle.

DESCRIPTION OF THE INVENTION

The present invention has as its object the formulation of new reactive monomers based on acrylates or methacrylates (referred to hereinafter individually and collectively as (meth)-acrylate compounds) which exhibit a number of desirable properties in their use and in the bondings which utilize them. These new monomers exhibit low volatility, based on their low vapor pressure. Despite their high molecular weight, they either exist as, or can be formulated into, a liquid or at least a viscous spreadable paste at room temperature. If they are solids at room temperature, they nonetheless exhibit good miscibility with the additional components normally used with adhesive systems. Additionally, use of the new monomers results in very strong elastic bonds.

The technical solution to the problems to which the present invention is directed is based on the fact that (meth)-acrylate derivatives of certain polyester-oligomers are able to optimally combine the desired technical effects.

The object of the present invention accordingly, in one of its first embodiments, relates to new (meth)-acrylate compounds with terminal (meth)-acrylic acid groups on an oligomer chain, which have low volatility and which are liquid to solid at room temperature, and wherein the oligomer chain is present as a polyester-oligomer that is formed from hydroxycarboxylic acids.

The new (meth)-acrylate compounds contain one or preferably two (meth)-acrylate groups on the polyester-oligomer chain. Also, mixtures of these types of compounds with one or with two (meth)-acrylate groups fall within the scope of the invention. For practical use, the more important types have two (meth)-acrylate groups in the molecule, wherein these functional groups are preferably situated terminally on the oligomer chain in such a manner that both terminal units (α, ω-positions) of the oligomer chain are each substituted with a (meth)-acrylate group.

The polyester-oligomer chain is formed from monohydroxy-monocarboxylic acids, wherein the oligomer chains contain the structural characteristic

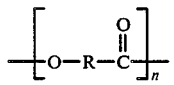

in which R is a straight or branched chain alkyl group, an unsubstituted or alkyl substituted cycloalkyl group, or an unsubstituted or alkyl substituted phenyl group, with R preferably having from 1 to 20 carbon atoms, more preferably from 2 to 10 carbon atoms, and most preferably from 2 to 7 carbon atoms; and n is an integer dependent on the selection of the R group, and is preferably chosen so that the mean molecular weight of the polyester-oligomer chain is in the range of from about 200 to about 600, more preferably about 300 to about 500.

The above polyester-oligomer chains are obtained through oligomerization of a hydroxycarboxylic acid, or a mixture of hydroxycarboxylic acids, of the formula

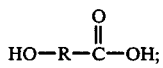

wherein R has the meaning given above. Especially important hydroxycarboxylic acids for the formation of these polyester-oligomer intermediates of the new (meth)-acrylate compounds are glycolic acid, the isomers of lactic acid, the isomers of α- or β-hydroxypropionic acid, the isomers of α-, β- or γ-hydroxybutyric acid, o-hydroxybenzoic acid (salicylic acid), m-hydroxybenzoic acid and/or p-hydroxybenzoic acid. Also, mixtures of two or more hydroxycarboxylic acids can be employed, in which case the R group defined above can have more than one structure in the polyester-oligomer chain, depending on the mixture of hydroxycarboxylic acids chosen for its preparation.

The polyester-oligomers are best prepared by the use of monofunctional and/or preferably by the use of difunctional coreactants, which fulfill a many faceted function. On the one hand, when using these reactants, control of the mean molecular weight of the polyester-oligomers and adjustment of the desired viscosity range is achieved. On the other hand, through the selection of the functional groups of the coreactants used it is possible to form on the polyester-oligomers uniform terminal hydroxyl groups or terminal carboxyl groups, which is normally not the case with polymers or oligomers of a hydroxycarboxylic acid. Finally, by using selected monofunctional coreactants, it is possible to eliminate one reactive terminal group of the polyester-oligomer, so that for this type of compound only one reactive function is available for the subsequent attachment of the (meth)-acrylate group. By suitable admixture of mono-functional and difunctional coreactants it is possible to obtain predetermined mixture ratios of mono-(meth)-acrylate compounds and bis-(meth)-acrylate compounds.

As the monofunctional coreactants, monoalcohols, mono-carboxylic acids, and/or monoamines, i.e. primary, secondary and/or tertiary monoamines, can be employed. Difunctional coreactants for the preparation of the polyester-oligomers are difunctional alcohols or dicarboxylic acids, or functionally reactive dicarboxylic acid derivatives, especially the corresponding anhydrides, esters, halides and the like.

If oligomers of the described type are prepared through cocondensation of hydroxycarboxylic acids and diols, there are obtained polyester-oligomers with terminal hydroxy groups. The quantity of diols used, together with the reaction conditions, determine the mean molecular weight of the resulting polyesteroligomers. On the other hand, if the oligomers are obtained through cocondensation of hydroxycarboxylic acids with dicarboxylic acids or reactive dicarboxylic acid derivatives, there is obtained polyester-oligomers with terminal carboxyl groups or derivatives of carboxyl groups. The coreactant acts as a control, standardizes the terminal reactive groups, and regulates the molecular weight. Information known in the art for the manufacture of polyesters or copolyesters is also applicable to the present process. The use of monoalcohols and/or monoamines will cause the desired blocking of the terminal carboxylic acid groups in the polyester-oligomers, while the use of monocarboxylic acids blocks the terminal hydroxyl group positions on the oligomers.

In all instances described herein, modified polyester-oligomers are formed which can be easily converted by known methods to (meth)-acrylate compounds. For example, if there are terminal hydroxyl groups on the polyester-oligomers, the (meth)-acrylic acid group is introduced through esterification or transesterification or by a comparable reaction with acrylic acids or acrylic acid esters and/or especially the corresponding methacrylic acid compounds. Also, if there are terminal carboxyl groups in the polyester-oligomers, the desired (meth)-acrylate group can readily be attached by known methods. Suitable here, for example, is the reaction of the oligomer intermediate product with glycidyl esters of acrylic acid or methacrylic acid. By splitting of the glycidyl group, the (meth)-acrylate group is attached via the glyceride group to the monocarboxylic or dicarboxylic acid formed as the intermediate.

In general, the selection of the monofunctional or difunctional coreactants, which are used herein in only minor amounts, can be made practically without limitations. These reactants can be based on saturated or olefinically unsaturated aliphatic or cycloaliphatic groups, or they can be aromatic in nature, e.g. phenyl or alkyl substituted phenyl. Generally, they do not contain more than 25 carbon atoms, and preferably not over 15. Suitable diols contain, for example, 2 to 20 carbon atoms, preferably 2 to 10, and more preferably 2 to 6 carbon atoms. The same limitations also apply for the corresponding dicarboxylic acids. Examples of suitable diols include ethylene glycol, diethylene glycol, triethylene glycol, tetraethylene glycol, propylene glycol, dipropylene glycol, 1,3-butylene glycol, 1,4-butylene glycol, 2,2-dimethyl-1, 3-propanediol, 2,2,4-trimethyl-1, 6-hexanediol, 1,4-cyclohexanedimethanol, 1,5-pentanediol, 1,6-hexanediol, 1,10-decanediol and 2,2-bis-(4-hydroxycyclohexyl)-propane.

Examples of dicarboxylic acids that can be employed include: oxalic acid, malonic acid, succinic acid, glutaric acid, adipic acid, pimelic acid, suberic acid, azelaic acid, sebacic acid, isosebacic acid, nonanedicarboxylic acid, decanedicarboxylic acid, undecanedicarboxylic acid, dodecanedicarboxylic acid, phthalic acid, hexahydrophthalic acid, isophthalic acid, terephthalic acid and biphenyldicarboxylic acid. As acid anhydrides, examples include: succinic anhydride, glutaric anhydride, phthalic anhydride, itaconic anhydride, citraconic anhydride, as well as alkenylsuccinic anhydrides.

It is understood that in all cases, i.e. for the hydroxycarboxylic acids as well as for the coreactants, not only the free reactive components of the type given above can be used, but also such reactive derivatives can be used which form by known methods under conditions of esterification or transesterification the desired polyester-oligomers of a predetermined molecular weight. Suitable in this connection are, for example, the esters of hydroxycarboxylic acids as well as lactones or lactams of hydroxycarboxylic acids, which when reacted with diols or diol esters can be transesterified. The manufacture of the polyester-oligomers as well as their conversion to the (meth)-acrylate compounds is carried out by known methods, for example, by reaction in the presence or in the absence of solvents and if desired in the presence of catalysts, especially esterification catalysts.

Within the scope of the invention are not only the difunctional (meth)-acrylate compounds described above, and not only the monofunctional (meth)-acrylate compounds described above, but also mixtures of difunctional and monofunctional (meth)-acrylate compounds. Should such mixtures of difunctional and monofunctional (meth)-acrylate compounds be desired, then in the preferred embodiment, the quantity of the monofunctional component is not in excess of 95 mole percent based on the mixture of the monofunctional and difunctional compounds. Preferred are mixtures thereof in which the content of monofunctional compounds is not over 50 mole percent, and preferably not over 10 mole percent.

The new (meth)-acrylate compounds are valuable constituents in reaction adhesives of known composition. Therefore, they are advantageously used in two component reaction adhesive systems of the type initially described above, i.e. where the other component (activator or hardener component) contains an initiator to initiate free radical polymerization. They can be used not only in conventional (meth)-acrylate systems but also in No-Mix adhesive systems. They are suitable for use in the so-called construction adhesives to bond metal, wood, glass, ceramics, and/or synthetic materials.

In a preferred embodiment of the invention, the new (meth)-acrylate compounds are flowable or, at least, still paste-like and spreadable at room temperature, and therefore they can be used as the main component or even as the sole polymerizable adhesive component in the reaction adhesives. It is thereby preferred that the liquid (meth)-acrylate compounds of the invention have a viscosity at room temperature in the range of from about 2000 to 70,000 mPas, preferably in the range of about 3000 to 50,000 mPas. Solid (meth)-acrylate compounds of the present type are readily soluble in liquid polymerizable components, such as methyl meth-acrylate, so that such solid compounds of the invention in admixture with liquid conventional monomer constituents are thereby converted in a simple manner to a technically desirable liquid adhesive component.

As is discussed above, as the initiator component for the polymerization and curing of adhesive systems, organoboron compounds can be used as well as systems based on benzoyl peroxide. The organoboron type initiators are all based on reactive boron components: they have the same reactivity as the known lower boron alkyls; however, they all show a definite decreased tendency for spontaneous ignition. This makes it possible to handle them easily and without danger. The organoboron compounds preferred for use herein show only a slow loss in activity when used in the presence of air. They can be used as separate hardener components in two component adhesive systems; it is also possible to use them as primers in systems of the so-called no-mix adhesives. The boron-containing hardeners preferred for use in the practice of the invention will guarantee high strength of the adhesive bond or of the in situ formed synthetic components. The rate of hardening can be controlled and therefore adjusted to the desired conditions of use. The structure of the initiator component guarantees good adhesion of the adhesives for bonding materials together. The hardeners of the invention to be used herein, based on organoboron compounds, are also described in the laid open European Patent Applications No. 81109074.5 (D 6144 EP) and No. 81109073.7 (D 6246 EP).

Especially important are the organoboron compounds and systems which are described in prior German Patent Applications Nos. D 6391 (P 31 43 945.4), D 6460 (P 32 01 780.4), D 6461 (P 32 01 731.6), D 6517 (P 32 07 264.3), and D 6548 (P 32 07 263.5).

Suitable initiators for the new systems can therefore be selected from the following groups of boron compounds:

(a) Boron alkyls with sterically hindered alkyl groups of the general formula

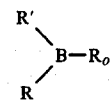

and

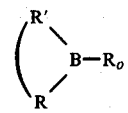

wherein R' and R are aliphatic monocyclic or dicyclic groups with 3 to 25 carbon atoms, and $R_o$ is hydrogen or a hydrocarbon group, preferably cyclic, having from 1 to 15 carbon atoms;

(b) boron compounds which are the reaction products of dihydroxy aromatic compounds with $BH_3$ or its alkylated products, having the general formula

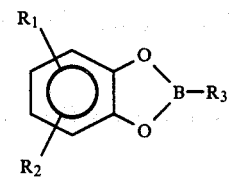

wherein $R_1$, $R_2$ and $R_3$ are either hydrogen or an alkyl group having 1 to 4 carbon atoms, and $R_1$ and $R_2$ can be an aromatic and/or an aliphatic cyclic group;

(c) boron compounds of the general formula

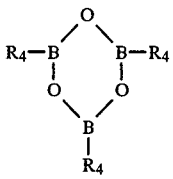

wherein R₄ is an alkyl group having 1 to 6 carbon atoms.

As boron alkyl compounds, there can be used a number of known boron alkyls which can be manufactured according to known methods. Typical representatives of such boron compounds are, for example, 9-borabicyclo[3.3.1]nonane, diisopinocampheyl borane, dicyclohexylborane, thexylborane(2,3-dimethyl-2-butylborane), 3,5-dimethylborinane, and diisoamylborane. From these compounds the first named 9-borabicyclo[3.3.1]nonane is preferred for practical reasons.

A compilation of possible methods for the preparation of these boron compounds can be found in the monograph by Herbert C. Brown, 1975 "Organic Synthesis via Boranes", Publisher John Wiley & Sons. As initiators there can be used hydroborated products of dialkylboranes and olefins. As olefins, there can be used butene, isobutene, hexene, cyclohexene, vinyl chloride, allyl chloride, allyl amine, methacrylic acid methyl ester, vinyl acetate, or crotonic acid methyl ester. Among the compounds suitable for use herein should be mentioned for example: diisopinocampheylbutyl boron, thexylcyclohexylcyclopentyl boron, thexyllimonyl boron, trinorbornyl boron, B-butyl-9-borabicyclo[3.3.1]nonane, B-isobutyl-9-borabicyclo[3.3.1]nonane, B-[2-(4-cyclohexenyl)-ethyl]-9-borabicyclo[3.3.1]nonane, B-cyclopropyl-9-borabicyclo[3.3.1]nonane, B-p-tolyl-9-borabicyclo[3.3.1]nonane, and B-tert.butyl-3, 5-dimethyl borinane. Additional products that are suitable for use herein are the reaction product of 1,2-dihydroxybenzene (pyrocatechol) with boron hydride (catechol borane), and tri-n-butylboroxin.

Additional especially preferred initiators or hardeners are described under (d) below:

(d) These starter systems of the invention consist of a homogeneous mixture of at least one organoboron compound which is activated by air, and an organic oligomer or polymer which is liquid to solid at room temperature and which is inert to the organoboron compound. The designation "homogeneous mixture" is understood to include single phase mixtures which are single phase at storage temperatures and use temperatures, which are characteristic of true solutions.

As organoboron compounds, there are suitable, first of all, boron alkyl and/or boron aryl compounds or the corresponding organoboron hydride compounds. Boron alkyl compounds or boron alkyl hydrides are an especially preferred class of materials. Preferred embodiments include compounds of the type:

R₁R₂R₃B, and/or R₁BH₂,

R₁R₂BH, wherein in these general formulas, the groups R₁, R₂ and R₃ are hydrocarbon groups, especially alkyl groups which can also include heteroatoms, especially O, N and/or S. If at least two such organic groups are attached to the boron atom, they can form a ring system of their own. The borons substituted with hydrocarbon groups, in their preferred embodiment, do not contain more than about 30 carbon atoms, preferably not more than about 25 carbon atoms. It is more preferred that each organic radical on the boron does not contain more than about 15 carbon atoms. As boron-containing initiator components, or for the preparation of suitable boron-containing initiator components, organoboron monohydride compounds, preferably the dialkylboron monohydrides, are particularly suitable for use.

A typical example of such boron compounds is, for example, 9-borabicyclo[3.3.1]nonane (9-BBN), which is listed under (a) above and is preferred for practical reasons. As boron initiators in this embodiment, there can also be used simple trialkylboranes such as hydroborated products of mono- or especially dialkyl boranes and olefins such as are described above.

As solvents with very low vapor pressures, there can be used oligomers or polymers which are inert toward the organoboron compounds. There are no restrictions with respect to the structure thereof provided that there is a homogeneous miscibility between those used as solvents and the organoboron compounds. Suitable, therefore, are all polymers, polycondensates and/or polyaddition products which fulfill the above requirements. The average molecular weight of these oligomers or polymers as solvents lie in the range of 200 to 50,000,000 grams/mole. Depending on structure and molecular weight, these solvents can have low viscosity and be flowable to solid at room temperatures. It is desirable that the mixtures of materials containing organoboron compounds be viscous, flowable, or spreadable at room temperature. However, this is not a prerequisite for the effectiveness of the starter systems used as initiators in accordance with this invention. On the contrary, the storage stability of the mixtures of materials which are solid at room temperature are particularly good. Suitable polymer solvents for use in this connection are, for example, polyethers, polyesters, polyamides, polyurethanes, polysiloxanes and the like. For the manufacture of flowable systems, there can be used oligomers that are liquid at room temperature having viscosities in the range of 1000 to 70,000 mPa's (room temperature) and these are especially interesting. The polyesters and the polyamides especially can be used in many ways in the practice of the invention. They can, as well as the other polymeric solvents, be manufactured according to known methods and, in this case, for example, through polycondensation of dicarboxylic acids with diols or diamines and, if desired or required, with the application of monofunctional reactants to modify or regulate the mean molecular weight. Preferred herein, as a rule, are saturated dicarboxylic acids and saturated glycols having up to 15 carbon atoms, preferably up to 10 carbon atoms in the molecule. In an analogous fashion, the above also applies to amines or diamines for the manufacture of polyamides. Suitable polyethers are, for example, polyethylene oxides or polypropylene oxides having a molecular weight in the required range. In this connection, a good knowledge of polymer chemistry is desirable. For the preparation of starter systems, the organoboron compounds are dissolved in the inert organic oligomers or polymers with complete exclusion of oxygen. If necessary, slight heat can be applied. It is, for example, possible in order to accelerate the dissolution to heat the mixture to a temperature up to 100° C., preferably about 70° C. When using oligomers or polymers that are solid at room temperature, the use of inert liquid solvents is suggested. Suitable are known solvents for organoboron compounds such as tetrahydrofuran or polyethers such as diethylene glycol dimethyl ether, or esters, halogenated hydrocarbons, and the like. When using these liquid adjuvants, after a homogeneous mixture is obtained the adjuvants are evacuated off, and the boron alkyl/oligomer mixture isolated. This mixture should be stored in closed vessels, preferably under an inert gas such as under nitrogen. The content of organoboron compounds in such starter systems is usually not over about 70% by weight and, preferably, not over about 50% by weight based on the total weight of the mixture. It is also preferred that the content of organoboron compounds is at least about 1 wt. % of the total weight of the system, so that quantities of about 1 to 50 wt. %, especially 3 to 50 wt. % are particularly suitable. Another important class of compounds for practical application involves the use of polymeric organoboron compounds as initiator components which are stabilized against exposure to air. These compounds are described under (e) below:

(e) the characteristics of this class of organoboron hardeners are that polymeric organoboron compounds are used which have as substituents on a polymer matrix, borane and/or organoboron groups stabilized against exposure to air. These boron-containing groups are preferably attached through B—C bonds to the polymer matrix. So long as the boron-containing groups are not the boryl group (—$BH_2$) itself, the boron-containing substituents in the polymer matrix in a further preferred embodiment have attached to the boron, with at least one additional B—C bond, one or two organic radicals. The preferred groups are hydrocarbon groups which can also contain heteroatoms, especially O, N and/or S. Suitable substituents on the boron are, in particular, alkyl, cycloalkyl and/or aryl groups which can be on one or both of the free valences of the boron which are not attached to the polymer matrix. When such organic groups other than hydrogen are in both boron valences, then they can together form a ring system. When compared to the usual boron alkyl hardeners, the oligomeric and polymeric boron compounds exhibit definite advantages. They are not self-igniting and have little requirements during storage. The activity of such hardeners remains even after long storage in air. The compatibility of the polymerizable components with the hardener can be assured by suitable selection of the polymer matrix in each instance. As a rule, for the hardening of the monomer components, the quantity of oligomeric or polymeric organoboron compounds required is very small.

These polymeric boron compounds can be obtained in a simple manner in that oligomers or polymers which contain addition receptive carbon double bonds undergo hydroboration, and consequently the boron-containing groups are introduced into at least a portion of the addition-receptive double bonds. Suitable for hydroboration are diborane as well as mono- or di-substituted boranes, that is, compounds of the general formula $R_4R_5BH$, wherein in this formula $R_4$ is an organic group, preferably a hydrocarbon group, and $R_5$ is a hydrogen or an organic group which can be the same as $R_4$ or different from $R_4$, or, together with $R_4$ and the boron, can form a ring system. The polymer matrix containing ethylenic double bonds, which are available for hydroboration, can be from low viscosity and flowable to solid, depending on their structure and molecular weight. Their mean molecular weight can have values of several million and is usually in the range of about 150 to about 3 million. Lower values within this range are normally preferred, especially those in the range of about 300 to about 500,000, and more especially in the range of about 500 to about 10,000. Also here it is desirable that the polymer matrix, and also the polymeric organoboron compounds obtained from them, be viscous to flowable or spreadable at room temperature. Here, for example, molecular weights of the polymer matrix in the range of about 300 to about 3,000 are especially suitable. For the effectiveness of the polymeric organoboron compounds used in the practice of the invention as initiators, this is not however a prerequisite. On the contrary, the storage stability of the polymeric organoboron compounds which are solid at room temperature are especially good.

The polymeric matrix prior to hydroboration can be ethylenically unsaturated to any degree. Preferred are matrix materials which prior to hydroboration have an iodine number in the range of about 1 to about 500, preferably about 5 to about 100, and more preferably about 8 to about 50.

Ethylenic double bonds available for hydroboration in the starting polymers can be in the main chain and/or in the side chain substituents.

The polymer matrix can have either a linear or branched structure, although polymeric materials with cross-linked structures are also possible for use herein.

As a polymeric matrix, all polymeric types are suitable so long as they contain double bonds which are available for hydroboration and contain no reactive groups which would lead to undesirable secondary reactions when the boron-containing groups are introduced into the polymeric material.

The polymeric material can also be obtained through polymerization or copolymerization of olefinically unsaturated components by polycondensation or by polyaddition reactions. Through suitable selection of polymers from synthesizable monomer types the desired amount of reactive double bonds for the subsequent hydroboration in the polymeric material is assured. Especially suitable as the polymer matrix are unsaturated oligomers or polymers which are obtained through a polycondensation reaction. Usable here are all the known polycondensate types such as polyesters, polyamides, polyimides, polycarbonates, polyurethanes and the like. Also suitable are oligomers or polymer types which have been obtained through polyaddition reactions. Details of the formation thereof can be found in earlier German Patent Application No. D 6461 (P 32 01 731.6).

The extent of hydroboration in the polymer matrix is limited only by the number of double bonds present. It has been found to be advantageous to have at least a substantial portion of these double bonds converted through the introduction of boron-containing substituents. In a preferred embodiment of this invention at least 30%, and preferably at least 50% of the orginally present ethylenic double bonds are hydroborated in the polymer matrix.

Especially suitable are such polymeric organoboron compounds wherein at least 80%, and preferably at least 90% or even at least 95% of the ethylenic double bonds have been reacted with the boron-containing component. A practically completely hydroborated material is in most cases the preferred initiator with respect to the practice of the invention. For hydroboration there can be used, in addition to diborane ($B_2H_4$), organoboron compounds with one or two organic groups, in particular, hydrocarbon groups. The preferred organic groups are alkyl, cycloalkyl, and/or aryl groups where two of the available groups together with the inclusion of the boron atom can form a ring. The substituted hydrocarbon groups preferably do not contain more than 25 carbon atoms, more preferably not more than about 15 carbon atoms.

An especially suitable class of organoboron compounds for the preparation of the polymeric initiator components are organoboronmonohydride compounds, especially dialkymonohydrides. A typical representative of such boron compounds is here also 9-borabicyclo[3.3.1]nonane, which is preferred for practical reasons.

A further interesting class of organoboron initiators are described as follows under (f):

(f) In this embodiment the substituted organoboron compounds are characterized in that the boronhydride group or organoboron group contains a fatty acid ester and/or a fatty alcohol ester. These boronalkyl compounds are hydroborated adducts of diborane and/or organoboron compounds with at least one B—H bond on fatty acid esters and/or fatty alcohol esters wherein at least one portion of the fatty acid group and/or fatty alcohol group contains carbon-carbon double bonds receptive to addition reactions.

Concerning the composition and preparation of this class of boronalkyl compounds, the following is applicable:

Esters or ester mixtures which serve as the matrix contain on B—C bonds as substituents boronhydride groups and/or organoboron groups. To the extent these boron-containing groups do not represent the boryl group ($-BH_2$) itself, such boron-containing substituents in a preferred embodiment have attached to the boron with at least one additional B—C bond one or two organic groups. Preferred groups are hydrocarbon groups, which can optionally contain heteroatoms, especially O, N, and/or S. Suitable substituents on the boron are preferably alkyl, cycloalkyl, and/or aryl groups, which are in one or both valences of the boron which are not attached to the ester matrix. In the event the organic groups other than hydrogen are on both boron valences, they can together form a ring system.

These boron compounds can be produced in a simple manner, when the starting material containing the ester matrix having olefinic double bonds has been subjected to hydroboration with diborane, or preferably with monosubstituted and especially with di-substituted boranes of the general formula $R_6R_7BH$, wherein in this formula $R_6$ is an organic group, preferably a hydrocarbon group, and $R_7$ is hydrogen or also an organic group, which can be the same as $R_6$ or different from $R_6$ or together with $R_6$ can form a ring system with the boron. Preferred organic groups are alkyl, cycloalkyl and/or aryl groups. The hydrocarbon groups which substitute the boron preferably contain not more than 25 carbon atoms, preferably not more than 15 carbon atoms. In an especially preferred embodiment, $R_6$ and $R_7$ together with the boron atom forms a ring system which does not exceed the above values for the number of carbon atoms. Here also the above mentioned 9-BBN is preferred for practical reasons. Of decisive importance is the ester base that serves as the matrix. The starting materials for this matrix are characterized in that they are monofunctional fatty acids and/or monofunctional fatty alcohols which are converted into esters or ester mixtures, wherein at least one portion of their fatty acid and/or fatty alcohol components have a carbon-carbon double bond receptive to addition reactions. The terms fatty acids and fatty alcohols encompass monofunctional components of the named type with a carbon atom number in the range of about 8 to 32 carbon atoms, preferably in the range of about 14 to 22 carbon atoms. The unsaturated fatty acids or unsaturated fatty alcohols can be of synthetic or natural origin. Preferably there are used singly or multiply olefinically unsaturated alkene monocarboxylic acids or monoalkenols of the required carbon number. The carbon chains of these fatty acids or fatty alcohols can be straight chain and/or branched.

The complementary components forming the esters can be either a monohydroxy or polyhydroxy alcohol or, respectively, a monofunctional or a polyfunctional carboxylic acid. It is possible to have the addition available carbon-carbon double bonds in only one constituent, i.e., only in the fatty acid or the fatty alcohol; however, both ester forming components can contain olefinic double bonds. For the preparation of the boron alkyl compounds used in the practice of the invention, at least substantial portion of these double bonds will be subjected to hydroboration. In a preferred embodiment, the ester matrix is formed through esterification of a monofunctional component (acid or alcohol) with a polyfunctional complementary component (alcohol or acid).

Especially preferred matrix materials are esters of unsaturated monocarboxylic acids (unsaturated fatty acids) with polyhydroxy alcohols. As the polyhydroxy ester-forming reaction component, especially suitable are those compounds which have a functionality up to 6, preferably with a functionality of 2 to 4. In this preferred embodiment for the matrix for the boron-containing substituents, monocarboxylic acids of the stated carbon number range are esterified with polyhydroxy alcohols, in particular with dihydroxy alcohols, trihydroxy alcohols, or tetrahydroxy alcohols.

It is advantageous to have the polyfunctional ester components with a relatively low number of carbon atoms which, for example, can be in the range of 2 to 10, preferably in the range of 2 to 6 carbon atoms. As polyfunctional alcohols, especially suitable are the lower glycols such as ethylene glycol, propylene glycol-1,2, propylene glycol-1,3, the $C_4$ glycols with terminal and/or internal hydroxyl groups, or the corresponding $C_5$ and $C_6$ compounds. An especially preferred alcohol for use herein is glycerine or polyhydroxy alcohols of the pentaerythrite type. On the other hand, monofunctional fatty alcohols can be esterified with lower polycarboxylic acids, in particular, with lower dicarboxylic acids or lower tricarboxylic acids.

It is also possible to use synthetic or natural fats and/or oils as the ester matrix for the subsequent hydroboration. Unsaturated esters in admixture with saturated components such as mixtures with saturated esters and/or in mixtures with different unsaturated esters can be used.

Esters of corresponding fats and/or oils which contain ethylenic double bonds available for hydroboration can be either low viscosity and flowable to solid depending on their structure and molecular weight.

The unsaturated esters or ester mixtures such as fats, oils and the like can be ethylenically unsaturated in various degrees prior to hydroboration. Preferred as suitable starting material are those having an iodine number of up to about 280, preferably in the range of about 1 to about 205. Within this range the value of the iodine number of from about 5 to about 130 is especially preferred.

The extent of hydroboration of the ester matrix can be selected freely within the framework of the total number of available double bonds. It has been proved advantageous when at least a substantial portion of these double bonds are converted by the introduction of the boron-containing substituents. In a preferred embodiment, more than 30%, preferably at least 50%, and more preferably at least 70% of the ethylenic double bonds of those originally available in the ester matrix are hydroborated. Especially preferred are those organoboron compounds in which, in relation to the reaction starting materials, at least 80%, preferably at least 90%, or even at least 95% of the ethylenic double bonds contain the boron-containing constituents.

For hydroboration, the unsaturated esters are reacted with the selected boronhydride compounds under complete exclusion of oxygen. It is advantageous here to work in the presence of solvents. Suitable are the known solvents for organoboron compounds, especially tetrahydrofuran, glycol, polyethers such as diethyleneglycol-dimethylether, esters, hydrogen halides, and the like. The reaction is preferably carried out in a temperature range of about 0° to about 100° C., preferably in the range of about room temperature to about 70° C.

In the following examples, which are given for illustration purposes only, there are described the preparation of various types of polyester-oligomers (Examples 1 to 10), then the preparation of the (meth)-acrylate derivatives of these polyester-oligomers (Examples 11 to 20) and, finally, the testing of these reactive monomers as construction adhesives (Example 21).

EXAMPLES 1-6

Oligohydroxycarboxylic acids with hydroxyl end groups (a) Preparation from glycolic acid and ethylene glycol In a three-necked flask equipped with stirrer and reflux condenser, glycolic acid and ethylene glycol are introduced under nitrogen. The mixture is heated quickly to 150° C. and then in the course of 6 hours from 150° to 200° C. During this time, the largest portion of the water of reaction separates, indicating the conversion of the ester condensation. The composition is allowed to cool to about 150° C., evacuated carefully to 10 Torr and the conversion is completed at 200° C. and 10 Torr. After 30 minutes, the product is removed hot at about 150° C. The composition of the starting materials and the properties of the oligomers obtained are given in Table 1 (Examples 1-3).

TABLE 1

Oligohydroxycarboxylic acids with terminal hydroxyl groups from glycolic acid and ethylene glycol

| | Adducts | | Reaction | | Calculated | |
|---|---|---|---|---|---|---|
| Example | Glycolic acid, moles | Ethylene glycol moles | water, % of theory | Acid number | Molecular Weight g/mole | Appearance |
| 1 | 3 | 1 | 100 | 14 | 252 | Clear, viscous, light yellow |
| 2 | 4 | 1 | >90 | 20 | 294 | Viscous, white |
| 3 | 6 | 1 | >98 | 24 | 410 | Wax-like, white |

(b) Preparation from lactic acid ethyl ester and ethylene glycol

In a three-necked flask equipped with stirrer and reflux condenser, lactic acid ethyl ester and ethylene glycol are combined. As catalyst, there is added 70 ml of 0.2% methanolic sodium methylate solution and the mixture is then heated to 150° C. The temperature is then carefully raised to 180° C., and at this temperature ethanol constantly distills off. After completion of the ethanol separation after about 16 hours, the flask is evacuated at a bath temperature of 150° C. at 10 Torr and the material remaining in the flask is then removed under nitrogen. The composition of the starting materials and the properties of the oligomers obtained are set forth in Table 2 (Examples 4-6).

TABLE 2

Oligohydroxycarboxylic acids with terminal hydroxyl groups from lactic acid ethyl ester and ethylene glycol

| | Adducts | | Products | | |
|---|---|---|---|---|---|
| Example | Lactic acid ethyl ester, moles | Ethylene glycol, moles | Yield Ethanol, % | Molec. Wt. | Appearance |
| 4 | 2 | 1 | 95 | 193 (Osmosis) | Clear, viscous, orange colored |
| 5 | 4 | 1 | 92 | — | Clear, viscous, brown |
| 6 | 6 | 1 | 96 | — | Clear, viscous, reddish brown |

EXAMPLES 7-10

Oligohydroxycarboxylic acids with terminal carboxyl groups

General Method (a) Through conversion of oligohydroxycarboxylic acids having terminal hydroxyl groups with succinic anhydride

EXAMPLE 7

206.3 grams of the oligomer of Example 4, 200 grams of succinic anhydride, and 1 gram of benzyltrimethylammonium methoxide (40% in methanol) are combined in a three-necked flask equipped with stirrer, reflux condensor, and nitrogen supply, and stirred for 8 hours at 80° C. under nitrogen. The product is characterized by the following coefficients:

Acid number: 296
OH number: <3

(b) Preparation from glycolic acid and adipic acid

In a three-necked flask equipped with stirrer and reflux condenser, the adipic acid and the glycolic acid are introduced. The mixture is heated rapidly under nitrogen to 150° C. and then during the course of 6 hours the temperature is raised from 150° C. to 200° C. During this procedure, the main portion of the water of reaction separates, which indicates the degree of completion of the ester condensation reaction. The mixture is cooled to about 150° C., carefully evacuated under 10 Torr and the reaction is completed at 200° C. and 10 Torr. The product is then removed while hot under nitrogen. The composition of the starting materials and the properties of the oligomers obtained are set forth in Table 3 (Examples 8-10).

TABLE 3

Oligohydroxycarboxylic acids with terminal carboxyl groups from glycolic acid and adipic acid

| | Adducts | | Products | | |
|---|---|---|---|---|---|
| | Glycolic acid, | Adipic acid, | Yield of water of reaction, | Acid | Molec. weight from acid number, |
| Example | moles | moles | % | number | g mole$^{-1}$ | Appearance |
| 8 | 1 | 1 | >99 | 620 | 181 | Wax-like, hard |
| 9 | 3 | 1 | >98 | 376 | 298 | Wax-like, soft |
| 10 | 4 | 1 | >96 | 334 | 336 | Wax-like, soft |

EXAMPLES 11-20

Oligohydroxycarboxylic acids with polymerizable end groups (a) Oligohydroxycarboxylic acids with polymerizable end groups from oligohydroxycarboxylic acids with terminal hydroxyl groups.

In a three-necked flask equipped with stirrer and water separator, the oligohydroxycarboxylic acids with terminal hydroxyl groups and 1.1 equivalents of methacrylic acid per hydroxyl group are introduced. At the same time—in relation to the methacrylic acid—equivalent quantities by weight of toluene and also 2% by weight each of p-toluenesulfonic acid and hydroquinone are added.

The mixture is heated with rapid stirring to the boiling point and the water of reaction formed is removed with a water separator.

If after 5 hours reaction time less than 90 to 95 weight % of the theoretical quantity of the theoretically expected water of reaction has separated, there is added once again 20% of the originally added quantity of methacrylic acid with 2 weight % each of paratoluenesulfonic acid and hydroquinone and the reaction is continued.

The reaction is completed when 90 to 95% of the expected water of reaction has formed. The reaction product after cooling is added to twice its volume of ethanol and filtered. The clear ethanolic solution is condensed to ¼ of its original volume with a rotation evaporator, then poured into the same quantity of water and neutralized with sodium hydrogen carbonate. The organic phase is separated, the aqueous phase shaken with toluene, the organic phases combined, washed three times with water, and dried over sodium sulfate. The solvent is evacuated at room temperature first in a rotation evaporator and then at $10^{-4}$ Torr. The composition of the starting materials and the properties of the polymerizable oligomers formed are set forth in Table 4 (Examples 11-16).

TABLE 4

Oligohydroxycarboxylic acids with polymerizable terminal groups

| Example | Diol adduct from Example | Yield of Water of Reaction, % | Appearance |
|---|---|---|---|
| 11 | 1 | >97 | Homogeneous, low viscosity liquid, brown |
| 12 | 2 | >95 | Homogeneous, low viscosity liquid, brown |
| 13 | 3 | >95 | Homogeneous, low viscosity liquid, brown |
| 14 | 4 | >95 | Homogeneous, low viscosity liquid, brown |
| 15 | 5 | >95 | Homogeneous, viscous, brown |
| 16 | 6 | >90 | Homogeneous, viscous, brown |

(b) Oligohydroxycarboxylic acids with polymerizable end groups from oligohydroxycarboxylic acids with terminal carboxyl groups In a three-necked flask equipped with stirrer and reflux condenser are placed the oligohydroxycarboxylic acid with terminal carboxyl groups and 1.0 equivalents of glycidyl methacrylate with 0.1% by weight benzyltrimethylammonium methoxide and 0.06% by weight of hydroquinone. With stirring, the mixture is heated within 45 minutes to 80° C. and the reaction continued at 80° C. until the acid number has dropped below 35. Normally the reaction goes to completion within 10 to 20 hours.

The composition of the starting material and the properties of the polymerizable oligomers are set forth in Table 5 (Examples 17-20).

TABLE 5

Oligohydroxycarboxylic acids with polymerizable end groups

| | Dicarboxylic acid adduct | Product | |
|---|---|---|---|
| Example | from Example | Acid number | Appearance |
| 17 | 7 | 24 | Homogeneous, viscous, yellow |
| 18 | 8 | 30 | Homogeneous, viscous, light yellow |
| 19 | 9 | 34 | Homogeneous, highly viscous, light yellow |
| 20 | 10 | 31 | Homogeneous, highly viscous, light yellow |

EXAMPLE 21

Construction bonding with oligohydroxycarboxylic acids with polymerizable end groups With the monomers prepared herein, sandblasted and degreased sheet iron (DIN 53,281/53,283) are used for bonding purposes. The oligohydroxycarboxylic acids with polymerizable end groups which are prepared herein are used
I. in pure form,
II. in a mixture of 20% by weight hydroxyethylmethacrylate,
III. in a mixture with 20% by weight methylmethacrylate and 5% by weight methacrylic acid.

(a) To each 5 grams of monomers (I) or the monomer mixtures (II, III) there were added, with intensive mixing, first 0.5% by weight N,N-dimethyl-p-toluidine and then 0.5% by weight of dibenzoylperoxide. The mixtures had pot times between 2 and 8 minutes. The sandblasted and degreased iron sheets were bonded with the adhesive and after 24 hour storage at room temperature in air, the stress shearing strengths were determined. In a further series of experiments, there was added to each 5 grams of monomers (I) or the monomer mixtures (II, III) 1% by weight of dibenzoylperoxide and to an additional 5 grams of monomer, 1% by weight of N,N-dimethyl-p-toluidine. One portion of the iron sheets were brushed with the peroxide-containing monomer and the other portion with the di-methyltoluidine-containing monomer.

Differently coated test sheets were paired together and fixed. The test sheets were stored for 24 hours at room temperature and then torn apart in a stress shearing test. The measured stress shearing values are listed in Table 6. The stress shearing values given are arithmetic means of 6 bondings each according to (a) and (b) at a stress shearing rate of 12 mm/minute.

TABLE 6

Stress shearing values for the bonding of iron sheets using monomer adhesives based on oligohydroxycarboxylic acids with polymerizable terminal groups/Nmm$^{-2}$.

| Monomer from Example | I | II Hydroxyethyl-methacrylate 20 wt. % | III Methylmethacrylate 20 wt. % methacrylic acid 5 wt. % |
|---|---|---|---|
| 11 | 15 | 16 | 18 |
| 12 | 17 | 20 | 18 |
| 13 | 18 | 18 | 19 |
| 14 | 13 | 15 | 16 |
| 15 | 16 | 16 | 17 |
| 16 | 8 | 16 | 16 |
| 17 | 11 | 18 | 20 |
| 18 | 17 | 21 | 22 |
| 19 | 7 | 24 | 23 |
| 20 | 6 | 21 | 19 |

What is claimed is:

1. A (meth)-acrylate compound having two terminal (meth)-acrylyl groups and a polyester oligomer chain that contains hydroxycarboxylic acid segments wherein the polyester oligomer chain has a mean molecular weight in the range of about 200 to about 600 and wherein the oligomer chain contains the structural characteristic

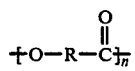

in which R has from 1 to 20 carbon atoms and is a straight or branched chain alkyl group, an unsubstituted or alkyl substituted cycloalkyl group, or an unsubstituted or alkyl substituted phenyl group, and n is an integer chosen to give a molecular weight for the oligomer chain in the above mean molecular weight range.

2. A (meth)-acrylate compound in accordance with claim 1 wherein the polyester oligomer chain has a mean molecular weight in the range of about 300 to about 500.

3. A (meth)-acrylate compounds in accordance with claim 1 wherein each hydroxycarboxylic acid segment present in the polyester oligomer chain contains from 2 to 10 carbon atoms.

4. A (meth)-acrylate compounds in accordance with claim 1 wherein each hydroxycarboxylic acid segment present in the polyester oligomer chain contains from 2 to 6 carbon atoms.

5. A (meth)-acrylate compound in accordance with claim 1 wherein each hydroxycarboxylic acid segment present in the polyester oligomer chain is formed from an acid selected from the group consisting of glycolic acid, lactic acid, hydroxypropionic acid, hydroxybutyric acid, and hydroxybenzoic acid.

6. A (meth)-acrylate compound in accordance with claim 1 wherein said compound also contains at least one moiety derived from a difunctional alcohol, a difunctional carboxylic acid, or the corresponding anhydrides, esters or halides.

7. A (meth)-acrylate compound in accordance with claim 6 wherein any such moiety present in said compound contains not more than 25 carbon atoms.

8. A (meth)-acrylate compound in accordance with claim 6 wherein any such moiety present in said compound contains not more than 15 carbon atoms.

9. A (meth)-acrylate compound in accordance with claim 6 wherein any such moiety present in said compound contains from 2 to 10 carbon atoms.

10. A (meth)-acrylate compound in accordance with claim 6 wherein any such moiety present in said compound contains from 2 to 6 carbon atoms.

11. A (meth)-acrylate compound in accordance with claim 6 wherein a mixture of a monofunctional compound and a difunctional compound is employed in the formation of the (meth)-acrylate compound, and wherein the monofunctional compound is used in quantities not over 50 mole percent of said mixture.

12. A (meth)-acrylate compound in accordance with claim 1 wherein said compound has a viscosity at room temperature of from about 2000 to about 70,000 mPas.

13. A (meth)-acrylate compound in accordance with claim 12 wherein the viscosity at room temperature is from about 3,000 to about 50,000 mPas.

14. A (meth)-acrylate compound which is a (meth)-acrylic acid ester having a (meth)-acrylate group on a polyester oligomer chain that contains hydroxycarboxylic acid segments wherein the polyester oligomer chain has a mean molecular weight in the range of about 200 to about 600, and which compound also contains a moiety derived from a monocarboxylic acid of functionally reactive derivative thereof.

15. A (meth)-acrylate compound in accordance with claim 14 wherein the (meth)-acrylate group is obtained by reaction of the terminal carboxy group of the polymer oligomer chain with a glycidyl ester of (meth)-acrylic acid.

16. A (meth)-acrylate compound containing two terminal (meth)-acrylyl groups and an internal structure containing a polyester oligomer chain that contains hydroxycarboxylic acid segments and at least one moiety derived from a member selected from the group consisting of a difunctional alcohol, a dicarboxylic acid, and a reactive derivative of a dicarboxylic acid, in which such moieties do not contain more than 25 carbon atoms, wherein said compound is prepared by the steps of (i) cocondensing at least one hydroxycarboxylic acid of the formula

wherein R is a straight or branched chain alkyl group, an unsubstituted or alkyl substituted cycloalkyl group, or an unsubstituted or alkyl substituted phenyl group, with a coreactant which is one or more of a member selected from the group consisting of a difunctional alcohol, a dicarboxylic acid, and the anhydrides, esters or halides of the corresponding dicarboxylic acid, wherein such coreactant does not contain more than 25 carbon atoms, to form an intermediate product containing either two terminal hydroxy groups, two terminal carboxyl groups, or one terminal hydroxy group and one terminal carboxyl group; and (ii) reacting any terminal hydroxy groups on the intermediate product with (meth)-acrylic acid or an ester thereof, and reacting any terminal carboxyl groups on the intermediate product with the glycidyl ester of (meth)-acrylic acid.

17. A (meth)-acrylate compound in accordance with claim 16 wherein the step (i) cocondensation is carried out with a hydroxycarboxylic acid and a difunctional alcohol.

18. A (meth)-acrylate compound in accordance with claim 16 wherein the step (i) cocondensation is carried out with a hydroxycarboxylic acid and a member selected from the group consisting of a dicarboxylic acid and a reactive derivative thereof.

19. A (meth)-acrylate compound in accordance with claim 16 wherein in step (i) the R group in the hydroxycarboxylic acid contains from 1 to 20 carbon atoms.

20. A (meth)-acrylate compound in accordance with claim 19 wherein the R group contains from 2 to 10 carbon atoms.

21. A (meth)-acrylate compound in accordance with claim 19 wherein the R group contains from 2 to 7 carbon atoms.

22. A (meth)-acrylate compound in accordance with claim 16 wherein in step (i) a mixture of two or more hydroxycarboxylic acids are employed therein.

23. A (meth)-acrylate compound in accordance with claim 16 wherein the compound has a viscosity at room temperature of from about 2,000 to 70,000 mPas.

24. A (meth)-acrylate compound in accordance with claim 23 wherein the viscosity is from about 3,000 to about 50,000 mPas.

25. A (meth)-acrylate compound in accordance with claim 16 wherein in step (i) the at least one hydroxycarboxylic acid is at least one acid selected from the group consisting of glycolic acid, an isomer of α or β-hydroxypropionic acid, an isomer of α-, β- or γ-hydroxybutyric acid, o-hydroxybenzoic acid, m-hydroxybenzoic acid, and p-hydroxybenzoicc acid.

26. A (meth)-acrylate compound in accordance with claim 16 wherein a mixture of a monofunctional compound and a difunctional compound is employed in step (i), and wherein the monofunctional compound is used in quantities not over 50 mol percent of said mixture.

27. A compound containing hydroxycarboxylic acid segments and at least one moiety derived from a member selected from the group consisting of a difunctional alcohol, a dicarboxylic acid, and the anhydrides, esters or halides of the corresponding dicarboxylic acid, in which such moieties do not contain more than 25 carbon atoms, wherein the compound is prepared by cocondensing at least one hydroxycarboxylic acid of the formula

wherein R is a straight or branched chain alkyl group, an unsubstituted or alkyl substituted cycloalkyl group, or an unsubstituted or alkyl substituted phenyl group, with a coreactant which is at least one of a member selected from the group consisting of a difunctional alcohol, a dicarboxylic acid, and a reactive derivative of a dicarboxylic acid wherein such coreactant does not contain more than 25 carbon atoms, to form a compound containing either two terminal hydroxy groups, two terminal carboxyl groups, or one terminal hydroxy group and one terminal carboxyl group.

28. A compound in accordance with claim 27 wherein the cocondensation is carried out with a hydroxycarboxylic acid and a difunctional alcohol.

29. A compound in accordance with claim 27 wherein the cocondensation is carried out with a hydroxycarboxylic acid and a dicarboxylic acid or the corresponding anhydrides, esters or halides.

30. A compound in accordance with claim 27 wherein the R group in the hydroxycarboxylic acid contains from 1 to 20 carbon atoms.

31. A compound in accordance with claim 30 wherein the R group contains from 2 to 10 carbon atoms.

32. A compound in accordance with claim 30 wherein the R group contains from 2 to 7 carbon atoms.

33. A compound in accordance with claim 27 wherein in forming the compound a mixture of two or more hydroxycarboxylic acids are employed therein.

34. A compound in accordance with claim 27 wherein the at least one hydroxycarboxylic acid is at least one acid selected from the group consisting of glycolic acid, an isomer of α- or β-hydroxypropionic acid, an isomer of α-, β- or γ-hydroxybutyric acid, o-hydroxybenzoic acid, m-hydroxybenzoic acid, and p-hydroxybenzoic acid.

35. A compound in accordance with claim 27 wherein a mixture of a monofunctional compound and a difunctional compound is employed in forming the compound, and wherein the monofunctional compound is used in quantities not over 50 mol percent of said mixture.

* * * * *

UNITED STATES PATENT AND TRADEMARK OFFICE
CERTIFICATE OF CORRECTION

PATENT NO. : 4,675,433

DATED : June 23, 1987

INVENTOR(S) : Wolfgang Ritter

It is certified that error appears in the above-identified patent and that said Letters Patent is hereby corrected as shown below:

The term of this patent subsequent to December 2, 2003 has been disclaimed.

Signed and Sealed this

Eighteenth Day of August, 1987

*Attest:*

DONALD J. QUIGG

*Attesting Officer*  *Commissioner of Patents and Trademarks*